United States Patent
Chin

(10) Patent No.: US 7,597,698 B2
(45) Date of Patent: Oct. 6, 2009

(54) APPARATUS AND METHOD FOR ENDOSCOPIC ENCIRCLEMENT OF PULMONARY VEINS FOR EPICARDIAL ABLATION

(75) Inventor: Albert K. Chin, Palo Alto, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 1008 days.

(21) Appl. No.: 10/618,140

(22) Filed: Jul. 10, 2003

(65) Prior Publication Data

US 2004/0216748 A1    Nov. 4, 2004

Related U.S. Application Data

(63) Continuation-in-part of application No. 10/369,980, filed on Feb. 18, 2003, now Pat. No. 7,288,096, which is a continuation-in-part of application No. 10/347,212, filed on Jan. 17, 2003, now abandoned, which is a continuation-in-part of application No. 10/346,663, filed on Jan. 17, 2003, now Pat. No. 7,264,587, which is a continuation-in-part of application No. 10/140,309, filed on May 6, 2002, which is a continuation of application No. 09/635,721, filed on Aug. 9, 2000, application No. 10/618,140, which is a continuation-in-part of application No. 09/779,715, filed on Feb. 8, 2001, now Pat. No. 6,569,082, which is a continuation of application No. 09/738,608, filed on Dec. 14, 2000, now abandoned, which is a continuation-in-part of application No. 09/635,345, filed on Aug. 9, 2000, now Pat. No. 7,398,781, application No. 10/618,140, which is a continuation-in-part of application No. 10/006,321, filed on Dec. 4, 2001, now Pat. No. 6,706,052, which is a continuation of application No. 09/915,695, filed on Jul. 25, 2001, now Pat. No. 6,428,556.

(60) Provisional application No. 60/148,130, filed on Aug. 10, 1999, provisional application No. 60/150,737, filed on Aug. 25, 1999.

(51) Int. Cl.
*A61B 17/32* (2006.01)
*A61B 18/14* (2006.01)

(52) U.S. Cl. .......................... 606/167; 606/41

(58) Field of Classification Search ................. 606/129, 606/198, 41; 600/37, 16–18, 374, 471, 674; 128/898; 607/122, 101, 116
See application file for complete search history.

(56) References Cited

U.S. PATENT DOCUMENTS 207,932 A     9/1878  Alvord (Continued)

FOREIGN PATENT DOCUMENTS

DE          39 42 589          12/1989

(Continued)

OTHER PUBLICATIONS

Bartoccioni, S., et al., Laparoscopic Harvesting of Right Gastroepipioic Artery for Coronary Artery Bypass Graft Performed Without Sternotomy [online], [retrieved on Oct. 5, 1999] Retrieved from the internet <URL:http://www.ctsnet.org/doc/2628.

(Continued)

*Primary Examiner*—Anhtuan T Nguyen
*Assistant Examiner*—Amy T Lang
(74) *Attorney, Agent, or Firm*—Law Office of Alan W. Cannon

(57) ABSTRACT

Surgical instruments and procedures promote placement of a tissue-ablating probe surrounding the left and right pulmonary veins within the intrapericardial space of a patient's heart via access through a subxiphoid or subcostal entry incision. An opening is formed in the pericardium near the apex region of the heart to facilitate formation of openings through three pericardial reflections by which a tissue-ablating probe is positioned around the pulmonary veins.

9 Claims, 6 Drawing Sheets

U.S. PATENT DOCUMENTS

| | | |
|---|---|---|
| 702,789 A | 6/1902 | Gibson |
| 1,727,495 A | 9/1929 | Wappler |
| 1,867,624 A | 7/1932 | Hoffman |
| 2,011,169 A | 8/1935 | Wappler |
| 2,028,635 A | 1/1936 | Wappler |
| 2,201,749 A | 5/1940 | Vandegrift |
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |
| 3,357,433 A | 12/1967 | Fourestier et al. |
| 3,856,016 A | 12/1974 | Davis |
| 3,870,048 A | 3/1975 | Yoon |
| 3,882,854 A | 5/1975 | Hulka et al. |
| 3,920,024 A | 11/1975 | Bowers |
| 3,934,115 A | 1/1976 | Peterson |
| RE29,088 E | 12/1976 | Shaw |
| 4,022,191 A | 5/1977 | Jamshidi |
| 4,181,123 A | 1/1980 | Crosby |
| 4,235,246 A | 11/1980 | Weiss |
| 4,270,549 A | 6/1981 | Heilman |
| 4,271,839 A | 6/1981 | Fogarty et al. |
| 4,291,707 A | 9/1981 | Heilman et al. |
| 4,318,410 A | 3/1982 | Chin |
| 4,319,562 A | 3/1982 | Crosby |
| 4,479,497 A | 10/1984 | Fogarty et al. |
| 4,493,711 A | 1/1985 | Chin et al. |
| 4,526,175 A | 7/1985 | Chin et al. |
| 4,630,609 A | 12/1986 | Chin |
| 4,662,371 A | 5/1987 | Whipple et al. |
| 4,765,341 A | 8/1988 | Mower et al. |
| 4,779,611 A | 10/1988 | Grooters et al. |
| 4,784,133 A | 11/1988 | Mackin |
| 4,863,440 A | 9/1989 | Chin |
| 4,921,483 A | 5/1990 | Wijay et al. |
| 4,957,477 A | 9/1990 | Lundback |
| 4,961,738 A | 10/1990 | Mackin |
| 4,991,578 A | 2/1991 | Cohen |
| 5,033,477 A | 7/1991 | Chin et al. |
| 5,071,428 A | 12/1991 | Chin et al. |
| 5,129,394 A | 7/1992 | Mehra |
| 5,131,905 A | 7/1992 | Grooters |
| 5,143,082 A | 9/1992 | Kindberg et al. |
| 5,150,706 A | 9/1992 | Cox et al. |
| 5,163,949 A | 11/1992 | Bonutti |
| 5,183,464 A | 2/1993 | Dubrul et al. |
| 5,183,465 A | 2/1993 | Xanthakos et al. |
| 5,215,521 A | 6/1993 | Cochran et al. |
| 5,246,014 A | 9/1993 | Williams et al. |
| 5,256,132 A | 10/1993 | Snyders |
| 5,271,380 A | 12/1993 | Riek et al. |
| 5,318,588 A | 6/1994 | Horzewski et al. |
| 5,318,589 A | 6/1994 | Lichtman |
| 5,331,975 A | 7/1994 | Bonutti |
| 5,334,150 A | 8/1994 | Kaali |
| 5,336,252 A | 8/1994 | Cohen |
| 5,339,801 A | 8/1994 | Poloyko et al. |
| 5,373,840 A | 12/1994 | Knighton |
| 5,376,076 A | 12/1994 | Kaali |
| 5,385,156 A | 1/1995 | Oliva |
| 5,391,156 A | 2/1995 | Hildwein et al. |
| 5,397,304 A | 3/1995 | Truckai |
| 5,411,517 A | 5/1995 | Guignard |
| 5,433,198 A | 7/1995 | Desai |
| 5,437,680 A | 8/1995 | Yoon |
| 5,453,094 A | 9/1995 | Metcalf et al. |
| 5,464,447 A | 11/1995 | Fogarty et al. |
| 5,482,925 A | 1/1996 | Hutsell |
| 5,496,345 A | 3/1996 | Kieturakis et al. |
| 5,514,153 A | 5/1996 | Bonutti |
| 5,540,711 A | 7/1996 | Kieturakis et al. |
| 5,551,947 A | 9/1996 | Kaali |
| 5,569,183 A | 10/1996 | Kieturakis |
| 5,569,291 A | 10/1996 | Privitera et al. |
| 5,569,292 A | 10/1996 | Scwemberger et al. |
| 5,571,161 A | 11/1996 | Starksen |
| 5,591,192 A | 1/1997 | Privitera et al. |
| 5,601,576 A | 2/1997 | Garrison |
| 5,601,589 A | 2/1997 | Fogarty et al. |
| 5,607,441 A | 3/1997 | Sierocuk et al. |
| 5,613,937 A | 3/1997 | Garrison et al. |
| 5,613,947 A | 3/1997 | Chin |
| 5,618,287 A | 4/1997 | Fogarty et al. |
| 5,630,813 A | 5/1997 | Kieturakis |
| 5,634,895 A | 6/1997 | Igo et al. |
| 5,650,447 A | 7/1997 | Keefer et al. |
| 5,653,722 A | 8/1997 | Kieturakis |
| 5,653,726 A | 8/1997 | Kieturakis |
| 5,667,472 A | 9/1997 | Finn et al. |
| 5,667,520 A | 9/1997 | Bonutti |
| 5,669,927 A | 9/1997 | Boebel et al. |
| 5,681,278 A | 10/1997 | Igo et al. |
| 5,685,820 A | 11/1997 | Riek et al. |
| 5,690,648 A | 11/1997 | Fogarty et al. |
| 5,695,504 A | 12/1997 | Gifford, III et al. |
| 5,702,343 A | 12/1997 | Alferness |
| 5,702,417 A | 12/1997 | Hermann |
| 5,707,390 A | 1/1998 | Bonutti |
| 5,713,950 A | 2/1998 | Cox |
| 5,716,392 A | 2/1998 | Bourgeois et al. |
| 5,722,977 A | 3/1998 | Wilhelmy |
| 5,725,492 A | 3/1998 | Igo et al. |
| 5,728,148 A | 3/1998 | Bostrom et al. |
| 5,730,756 A | 3/1998 | Kieturakis |
| 5,738,628 A | 4/1998 | Sierocuk et al. |
| 5,755,764 A | 5/1998 | Schroeppel |
| 5,755,765 A | 5/1998 | Hyde et al. |
| 5,762,604 A | 6/1998 | Kieturakis |
| 5,772,680 A | 6/1998 | Kieturakis et al. |
| 5,797,946 A | 8/1998 | Chin |
| 5,800,449 A | 9/1998 | Wales |
| 5,810,878 A | 9/1998 | Burel et al. |
| 5,827,216 A | 10/1998 | Igo et al. |
| 5,860,997 A | 1/1999 | Bonutti |
| 5,897,586 A | 4/1999 | Molina |
| 5,900,433 A | 5/1999 | Igo et al. |
| 5,902,331 A | 5/1999 | Bonner et al. |
| 5,904,711 A | 5/1999 | Flom et al. |
| 5,931,810 A | 8/1999 | Grabek |
| 5,957,835 A | 9/1999 | Anderson et al. |
| 5,957,880 A | 9/1999 | Igo et al. |
| 5,972,010 A | 10/1999 | Taheri |
| 5,972,012 A | 10/1999 | Ream et al. |
| 5,972,013 A | 10/1999 | Schmidt |
| 5,972,020 A | 10/1999 | Carpentier et al. |
| 5,980,548 A | 11/1999 | Evans et al. |
| 6,007,546 A | 12/1999 | Snow et al. |
| 6,010,531 A | 1/2000 | Donlon et al. |
| 6,019,777 A | 2/2000 | Mackenzie |
| 6,030,365 A | 2/2000 | Laufer |
| 6,030,406 A | 2/2000 | Davis et al. |
| 6,036,714 A | 3/2000 | Chin |
| 6,039,748 A | 3/2000 | Savage et al. |
| 6,048,337 A | 4/2000 | Svedman |
| 6,068,621 A | 5/2000 | Balceta et al. |
| 6,077,218 A | 6/2000 | Alferness |
| 6,080,174 A | 6/2000 | Dubrul et al. |
| 6,085,754 A | 7/2000 | Alferness et al. |
| 6,095,968 A | 8/2000 | Snyders |
| 6,096,064 A | 8/2000 | Routh |
| 6,102,046 A | 8/2000 | Weinstein et al. |
| 6,126,590 A | 10/2000 | Alferness |
| 6,132,456 A | 10/2000 | Sommer et al. |

| | | | |
|---|---|---|---|
| 6,139,522 A | 10/2000 | Weldon et al. | |
| 6,156,009 A | 12/2000 | Grabek | |
| 6,162,195 A | 12/2000 | Igo et al. | |
| 6,165,183 A | 12/2000 | Kuehn et al. | |
| 6,206,004 B1 | 3/2001 | Schmidt et al. | |
| 6,237,605 B1 * | 5/2001 | Vaska et al. | 128/898 |
| 6,267,763 B1 | 7/2001 | Castro | |
| 6,287,250 B1 | 9/2001 | Peng et al. | |
| 6,315,778 B1 | 11/2001 | Gambale et al. | |
| 6,322,536 B1 | 11/2001 | Rosengart et al. | |
| 6,346,074 B1 | 2/2002 | Roth | |
| 6,428,556 B1 | 8/2002 | Chin | |
| 6,463,332 B1 | 10/2002 | Aldrich | |
| 6,478,028 B1 | 11/2002 | Paolitto et al. | |
| 6,488,689 B1 | 12/2002 | Kaplan et al. | |
| 6,569,082 B1 | 5/2003 | Chin | |
| 6,607,547 B1 | 8/2003 | Chin | |
| 6,612,978 B2 | 9/2003 | Lau et al. | |
| 6,689,048 B2 | 2/2004 | Vanden Hoek et al. | |
| 6,697,677 B2 | 2/2004 | Dahl et al. | |
| 6,702,732 B1 | 3/2004 | Lau et al. | |
| 6,706,052 B1 | 3/2004 | Chin | |
| 6,835,193 B2 | 12/2004 | Epstein et al. | |
| 6,889,091 B2 | 5/2005 | Hine et al. | |
| 2001/0047147 A1 | 11/2001 | Slepian et al. | |
| 2002/0035361 A1 | 3/2002 | Houser et al. | |
| 2002/0052602 A1 | 5/2002 | Wang et al. | |
| 2002/0058925 A1 | 5/2002 | Kaplan et al. | |
| 2002/0111637 A1 | 8/2002 | Kaplan et al. | |
| 2002/0173622 A1 | 11/2002 | Wettstein et al. | |
| 2002/0177207 A1 | 11/2002 | Sugiyama et al. | |
| 2003/0212446 A1 | 11/2003 | Kaplan et al. | |
| 2008/0045946 A1 * | 2/2008 | Vaska | 606/49 |

FOREIGN PATENT DOCUMENTS

| | | |
|---|---|---|
| EP | 0095727 A1 | 12/1983 |
| EP | 0 642 764 | 9/1994 |
| EP | 0791330 A2 | 8/1997 |
| EP | 0938871 A2 | 9/1999 |
| FR | 1 370580 | 8/1964 |
| GB | 2 082 459 | 8/1981 |
| GB | 2 195 540 | 9/1987 |
| SU | 510235 | 4/1976 |
| SU | 1371689 | 3/1986 |
| WO | WO 00/25850 A1 | 5/0000 |
| WO | WO 96/00038 | 1/1996 |
| WO | WO 96/32882 | 10/1996 |
| WO | WO97/26831 | 7/1997 |
| WO | WO 98/24378 | 6/1998 |
| WO | WO 98/24488 A2 | 6/1998 |
| WO | WO 98/24488 A3 | 6/1998 |
| WO | WO 99/13785 | 3/1999 |
| WO | WO 99/13936 | 3/1999 |
| WO | WO 02/04064 A1 | 1/2002 |

OTHER PUBLICATIONS

Benetti, Federico, et al., "Video Assisted Coronary Bypass Surgery", J Card Surgery, 1995, pp. 620-625.
Bernhard, Victor M. et al., "Cardiovascular Endoscopy: Historical Perspectives", Endovascular Surgery, 1989 W.B. Saunders Company, pp. 13-30.
Broadman, R. et al., "ICD Implantation via Thoracoscopy, "Mailslot" Thoracotomy, and Subxiphoid Incision," The Annals of Thoracic Surgery, vol. 57, No. 2, Feb. 1994, pp. 475-476.
Carpentier, A, "Technique d'implantation de pace-maker par une voie d'abord abdominate sous-xyphoidienne," La Presse Medicate, Masson et Cie, Esiteurs, Paris, vol. 76, No. 2, Jan. 13, 1968, 2 pp.
Comedicus Gets Approvalto Sell Product in European Union, Mar. 1, 1999, Swenson NHB Investor Relations, 4 pages.
De Feyter, P.J. et al., "Permanent Cardiac Pacing with Suturetess Myocardial Electrodes: Experience in First One Hundred Patients," PACE, vol. 3, No. 2, Mar. 1980, pp. 144-149.
Delaria, G.A. et al., "Leg Wound Complications Associated With Coronary Revascularization", J. Thorac. Cardiovasc. Surgery. 81:403-407, 1981.
Dimitri, W.R., et al., "A Quick and Atraumatic Method of Autologous Vein Harvesting Using the Subcutaneous Extratuminal Dissector", J. Cardiovasc. Surg., 28:103-11, 1987.
Fogarty, M.D., Thomas J., et al., "Selected Applications of Baloon Dissection", pp. 45-52.
Fontenelle, Larry, J., "Subxiphoid Pericardial Window", Thoracic and Cardiovascular Surgery, The American Association for Thoracic Surgery, Jul. 1971, vol. 62, No. 1, pp. 95-97.
Grandjean, Jan G., et al., "Coronary Reoperation via Small Laparotomy Using Right Gastroepiptoic Artery Without CPB", Society of Thoracic Surgeons, 1996, pp.
Hauer, G., et al. "Endoscopic Subfascial Discussion of Perforating Vein", Surg. Endos. 2:5-12, 1988.
Kaminski, Diane, "Firm Aims to Bypass Heart-piercing Treatments", Medical Industry Today, Medical Data International. Sep. 23, 1998.
"Incision Decision", Atrium Medical Corporation advertisement, appearing in J. Thorac. Cardiovasc. Surg., 83(4), 1982.
Kirklin, John W., et al., "Cardiac Surgery: Morphology, Diagnostic Criteria, Natural History, Techniques, Results, and Indications", vol. 2, Second Edition, 1993, Chapter 52, p. 1695.
Levin. Bradley H., "The Subxiphoid Pericardial Window", Surgery, Gynecology & Obstetrics, Dec. 1982, vol. 155, pp. 804-806.
Meldrum-Hanna, W. et al., "Long Saphenous Vein Harvesting," J. Surg., 56: 923-924, 1986.
Moazami, N., M.D. et al., "Minimally Invasive Greater Saphenous Vein Harvesting For Coronary Artery Bypass Surgery", Mar. 1997, pp. 94-98.
Prager, Richard L., et al., "The Subxiphoid Approach to Pericardial Disease", The Annals of Thoracic Surgery, vol. 34, No. 1, Jul. 1982.
Rashid, A., et al., "Subcutaneous Techniques for Saphenous Vein Harvest", Ann. Thorac. Surg., 37(2):169-170, 1984.
Sabiston, David C., Jr., et al., "Atlas of Cardiothoracic Surgery", W.B. Saunders Company, 1995, pp. 235-237.
Santos, Gil H., et al., "The Subxiphoid Approach in the Treatment of Pericardial Effusion", Albert Einstein College of Medicine, Sep. 21, 1976, pp. 467-470.
"Saphenous Vein Grafts Are No. 1, Period," Atrium Medical Corporation advertisement, appearing in J. Thorac. Cardiovas. Surg., 82(6), 1981.
Simonsen, Michael, Ph.D., "Researchers Undaunted by Setbacks in the Angiogenesis Sector", American Health Consultants, vol. 5, No. 5, May 1999.
Spodick, David H., "Directly Applied Cardiac Therapy: Experts Explore Potential Benefits", Internal Medicine World Report, 1998.
Spodick, David H., "IPTD: Intrapericardial Therapeutics and Diagnostics: The PerDUCER Permits Direct Access to the Heart", Cath-Lab Digest, Sep. 1999, vol. 7, No. 9.
Stewart, S., M.D., "Placement of the Sutureless Epicardial Pacemaker Lead by the Subxiphoid Approach," The Annals of Thoracic Surgery, vol. 18, No. 3, Sep. 1974, pp. 308-313.
The 4th International Symposium on Intrapericardial Therapeutics and Diagnostics. Mar. 6, 1999, New Orleans, Louisiana.
Watkins, Jr., L., M.D. et al., "Implantation of the Automatic Defibrillator: The subxiphoid Approach," The Annals of Thoracic Surgery, vol. 34, No. 5, Nov. 1982, pp. 515-520.
Wheatley, D.J., M.D., ed., "Surgery of Coronary Artery Disease", C.V. Mosby Company, pp. 348-349, pp. 374-375.
Zenati, M., M.D. et al., "Left Heart Pacing Lead Implantation Using Subxiphoid Videopericardioscopy," J. Cardiovasc Electrophysiol, vol. 14, Sep. 2003, pp. 949-963.
PCT International Search Report and Written Opinion, PCT/US04/00875, Nov. 7, 2007, 7 pages.
PCT International Search Report and Written Opinion, PCT/US04/22137, Jul. 9, 2007, 8 pages.
European Supplementary Search Report, European Application No. 03724371.4, Jan. 27, 2009, 3 pages.

* cited by examiner

APPARATUS AND METHOD FOR ENDOSCOPIC ENCIRCLEMENT OF PULMONARY VEINS FOR EPICARDIAL ABLATION

RELATED APPLICATIONS

This application is a continuation-in-part of application Ser. No. 10/369,980, entitled "Subxiphoid Procedures And Apparatus For Placement Of Cardiac Defibrillator And Pacer", filed on Feb. 18, 2003 now U.S. Pat. No. 7,288,096 by Albert K. Chin, which is a continuation-in-part application of application Ser. No. 10/347,212, entitled "Apparatus And Methods For Endoscopic Surgical Procedures", filed on Jan. 17, 2003 now abandoned by Albert K. Chin, and which is also a continuation-in-part of application Ser. No. 10/346,663 entitled "Endoscopic Subxiphoid Surgical Procedures", filed on Jan. 17, 2003 now U.S. Pat. No. 7,264,587 by Albert K. Chin, et al., which is a continuation-in-part of pending application Ser. No. 10/140,309 entitled "Methods And Apparatus For Endoscopic Cardiac Surgery", filed on May 6, 2002 by Albert K. Chin, et al., which is a continuation of pending application Ser. No. 09/635,721 entitled "Apparatus For Endoscopic Access", filed on Aug. 9, 2000, which claims the benefit of provisional applications Ser. No. 60/148,130 filed on Aug. 10, 1999 and Ser. No. 60/150,737 filed on Aug. 25, 1999. This application is also a continuation-in-part application of pending application Ser. No. 09/779,715 entitled "Apparatus And Methods For Cardiac Restraint", filed on Feb. 8, 2001 now U.S. Pat. No. 6,569,082 by Albert K. Chin which is a continuation of pending application Ser. No. 09/738,608 entitled "Apparatus And Methods For Cardiac Restraint", filed on Dec. 14, 2000 now abandoned by Albert K. Chin, which is a continuation-in-part of pending application Ser. No. 09/635,345, entitled "Apparatus And Method For Subxiphoid Endoscopic Access", filed on Aug. 9, 2000 by Albert K. Chin, which claims the benefit of the aforecited provisional applications. This application is also a continuation-in-part of pending application Ser. No. 10/006,321 entitled "Longitudinal Dilator and Method", filed on Dec. 4, 2001 now U.S. Pat. No. 6,706,052 by Albert K. Chin, which is a continuation of pending application Ser. No. 09/915,695 entitled "Longitudinal Dilator And Method", filed on Jul. 25, 2001 by Albert K. Chin and now issued as U.S. Pat. No. 6,428,556, which claims the benefit of the aforecited provisional application Ser. No. 60/150,737, filed on Aug. 25, 1999. All applications are incorporated herein in their entireties by these references to form a part hereof.

FIELD OF THE INVENTION

This invention relates to methods and apparatus for ablating tissue about the pulmonary veins with diminished risk of collateral injury during placement of an ablation probe or sheath therefor.

BACKGROUND OF THE INVENTION

One clinically recognized treatment for chronic atrial fibrillation includes ablating the tissue surrounding the pulmonary vein ostia at the site in the intrapericardial space where the veins enter into the atria. Cardiac surgeons have described entering the chest through multiple thoracotomy incisions, using an endoscope and endoscopic instruments to dissect a tract under the superior vena cava and the inferior vena cava, and threading an ablation probe around the four pulmonary veins. In some of these cases, a surgical robot has been used to assist in the procedure. The probe enters posterior to the superior vena cava, winds through the transverse sinus of the pericardium, loops around the four pulmonary veins, and exits the tract that was dissected posterior to the inferior vena cava. The tract formed posterior to the superior vena cava enters into the transverse sinus of the pericardium. The tract formed posterior to the inferior vena cava completes the path of the ablation probe around the pulmonary veins.

In another technique to perform robotic probe placement endoscopically, one endoscope is advanced through a thoracotomy incision, or other entry incision, into the intrapericardial space adjacent the superior vena cava, and an endoscopic tool is inserted into the right pleural cavity via another thoracotomy incision. This latter endoscopic tool in the right pleural cavity is used to dissect through the right medial pleura and the pericardium posterior to the superior vena cava while being viewed with the endoscope. It is desirable to perform an ablation procedure using one set of endoscopic equipment and one endoscopic cannula.

In addition, encirclement of all four pulmonary veins with an epicardial ablation probe is hampered by two folds (known as reflections) of pericardium. One pericardial reflection forms the end of the transverse pericardial sinus and extends between the superior vena cava and the right superior pulmonary vein. The other pericardial reflection extends between the inferior vena cava and the right inferior pulmonary vein. It is relatively easy to dissect through the latter pericardial reflection, using an endoscopic subxiphoid cannula and a pericardial entry instrument. With the endoscopic subxiphoid cannula placed behind the heart in the oblique pericardial sinus, the pericardial reflection between the inferior vena cava and the right inferior pulmonary vein may be grasped by a pericardial entry instrument under endoscopic visualization, and an opening created through the reflection.

With the pericardial reflection between the superior vena cava and the right superior pulmonary vein, access is more difficult because this reflection forms the end of the transverse pericardial sinus and there is no direct way for the endoscopic subxiphoid cannula to approach this pericardial reflection. Without direct access and good visualization of this pericardial reflection, dissection is hazardous because the superior vena cava, right superior pulmonary vein, and right main pulmonary artery are all in the vicinity of the reflection. Grasping and forming a hole in the wrong structure, for example, the superior vena cava, would be disastrous.

SUMMARY OF THE INVENTION

In accordance with one embodiment of the present invention a procedure for traversing the pericardial reflection between the superior vena cava and the right superior pulmonary vein includes positioning an endoscopic subxiphoid cannula to place an ablation probe or a sheath into the transverse pericardial sinus and advance the ablation probe or sheath to the end of the transverse sinus. The endoscopic subxiphoid cannula is removed from the body, leaving the ablation probe or sheath in place, and is then reinserted and advanced to the oblique pericardial sinus. A pericardial entry instrument is inserted into the working channel of the subxiphoid cannula and used to grasp the pericardial reflection that forms the floor or base of the transverse pericardial sinus. When the floor of the transverse pericardial sinus is entered, the ablation probe or sheath should be visible. The ablation probe or sheath is pulled partially out of the transverse pericardial sinus, allowing the endoscopic subxiphoid cannula to visualize the pericardial reflection at the end of the transverse sinus. The pericardial entry instrument is used to grasp and form an opening through this reflection, and the grasper of the pericardial entry instrument grasps the ablation probe or sheath and advances it through the opening and laterally to the right superior and inferior pulmonary veins. The endoscopic subxiphoid cannula is then positioned in the oblique pericardial sinus, and the pericardial entry instrument is used to create an opening in the pericardial reflection between the inferior vena cava and the right inferior pulmonary veins. The ablation probe or sheath, now lying lateral to the right superior and inferior pulmonary veins, is grasped by the graspers of the entry instrument and pulled into the oblique pericardial sinus to complete the encirclement of all four pulmonary veins.

In accordance with another embodiment of the present invention, an endoscopic subxiphoid cannula is inserted via a left subcostal incision instead of a subxiphoid incision. The apex of the human heart lies in the left chest rather than at the midline. An incision approximately 1 cm below the left costal margin, at approximately the midclavicular line, may enable a closer, more direct access to the apex of the heart with the endoscopic subxiphoid cannula. With this technique, a 1.5-2.0 cm incision is made 1 cm below the costal margin. The anterior rectus sheath is incised, the rectus muscle is spread bluntly to expose the posterior rectus sheath, and a 1.5-2.0 cm incision is performed in the posterior rectus sheath. A gloved finger is inserted in the incision and advanced to the inferior border of the costal margin. The endoscopic subxiphoid cannula is inserted in the subcostal incision and advanced through the muscular fibers of the diaphragm into the left pleural cavity. The apex of the heart is identified, and the pericardial entry instrument is used to grasp the pleura overlying the apex and create an opening in the pleura to expose the pericardium. The pericardium is grasped with the pericardial entry instrument and is cut to form an access opening through the pericardium. The tapered conical tip of the endoscopic subxiphoid cannula is inserted through the pericardial opening to access the heart during the procedure previously described.

DETAILED DESCRIPTION OF THE INVENTION

Figure 1:
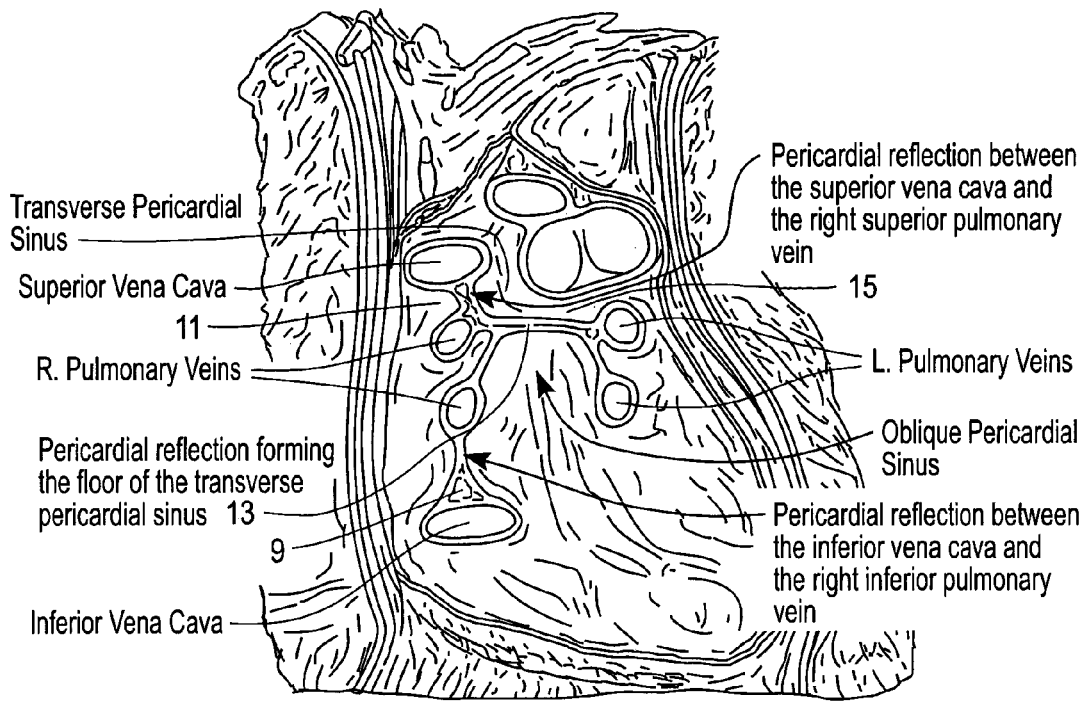
FIG. 1 is an anatomical view of the pericardial sac with the heart removed to illustrate the sinuses and reflections about the pulmonary veins.

Referring now to the simplified anatomical illustration of FIG. 1, there is shown a view of the pericardial sac (with the heart absent), as viewed frontally. In this view, there is shown the reflection 9 disposed between the inferior vena cava and the right inferior pulmonary vein. Additionally, this view shows the reflection 11 disposed between the superior vena cava and the right superior pulmonary vein. Also, this view shows the reflection 13 that forms the base of the transverse pericardial sinus 15. The objective of the surgical procedure performed in accordance with an embodiment of the present invention is to encircle the right and left pulmonary veins with a tissue-ablation probe (or sheath through which the ablation probe may be positioned) in order to ablate atrial tissue along a path substantially encircling the ostia of these veins. This is accomplished with diminished risk of penetration of the veins and arteries in the vicinity and with minimal damage or trauma to adjacent tissue. As used herein, a 'reflection' is a fold of tissue, in this case, the pericardium, that may form a barrier between sinuses or regions within the intrapericardal space.

Figures 2A, 2B:
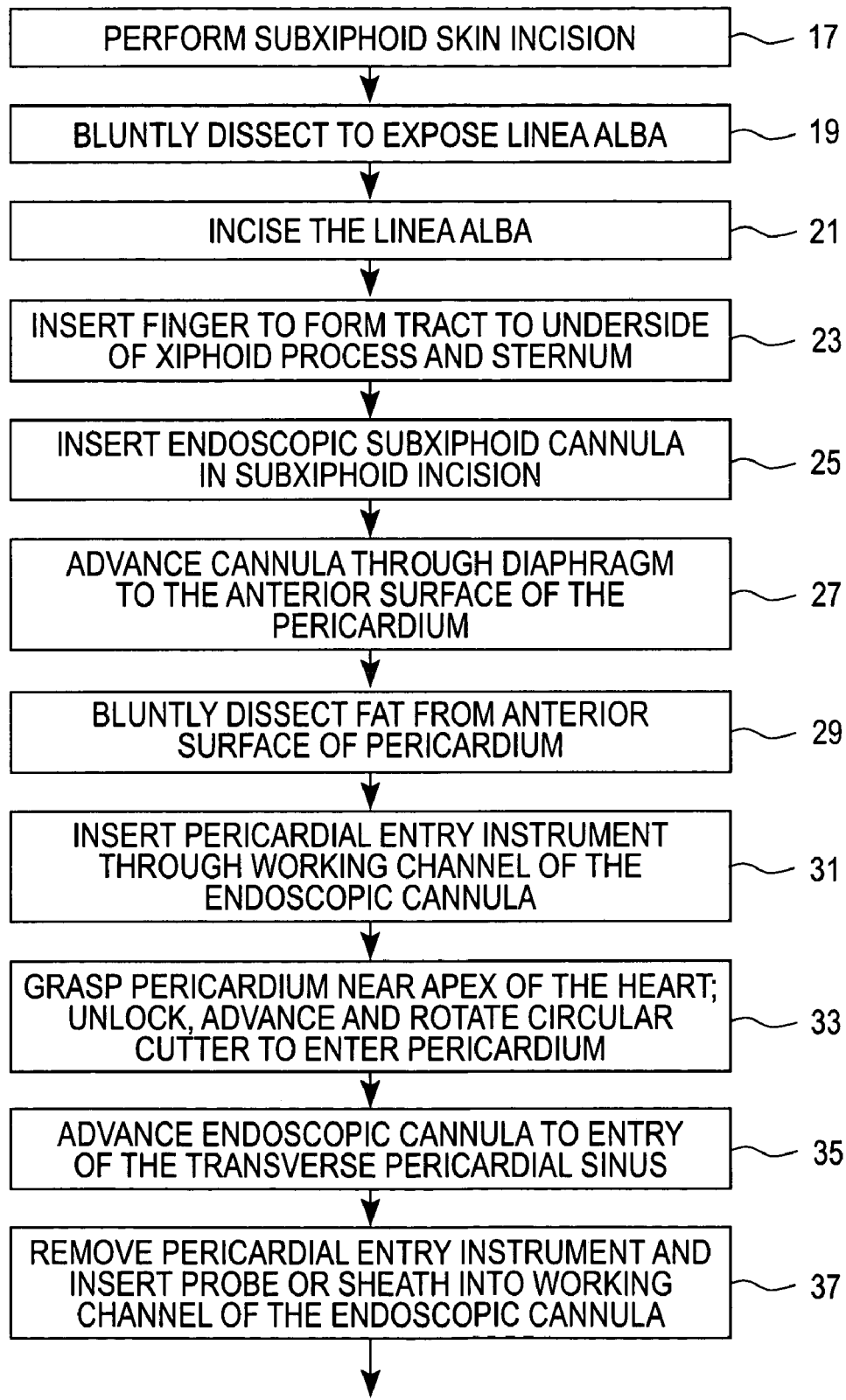
FIGS. 2*a*, *b*, *c* comprise a flow chart of a surgical procedure performed in accordance with the present invention via a subxiphoid entry.
Figure 2B:
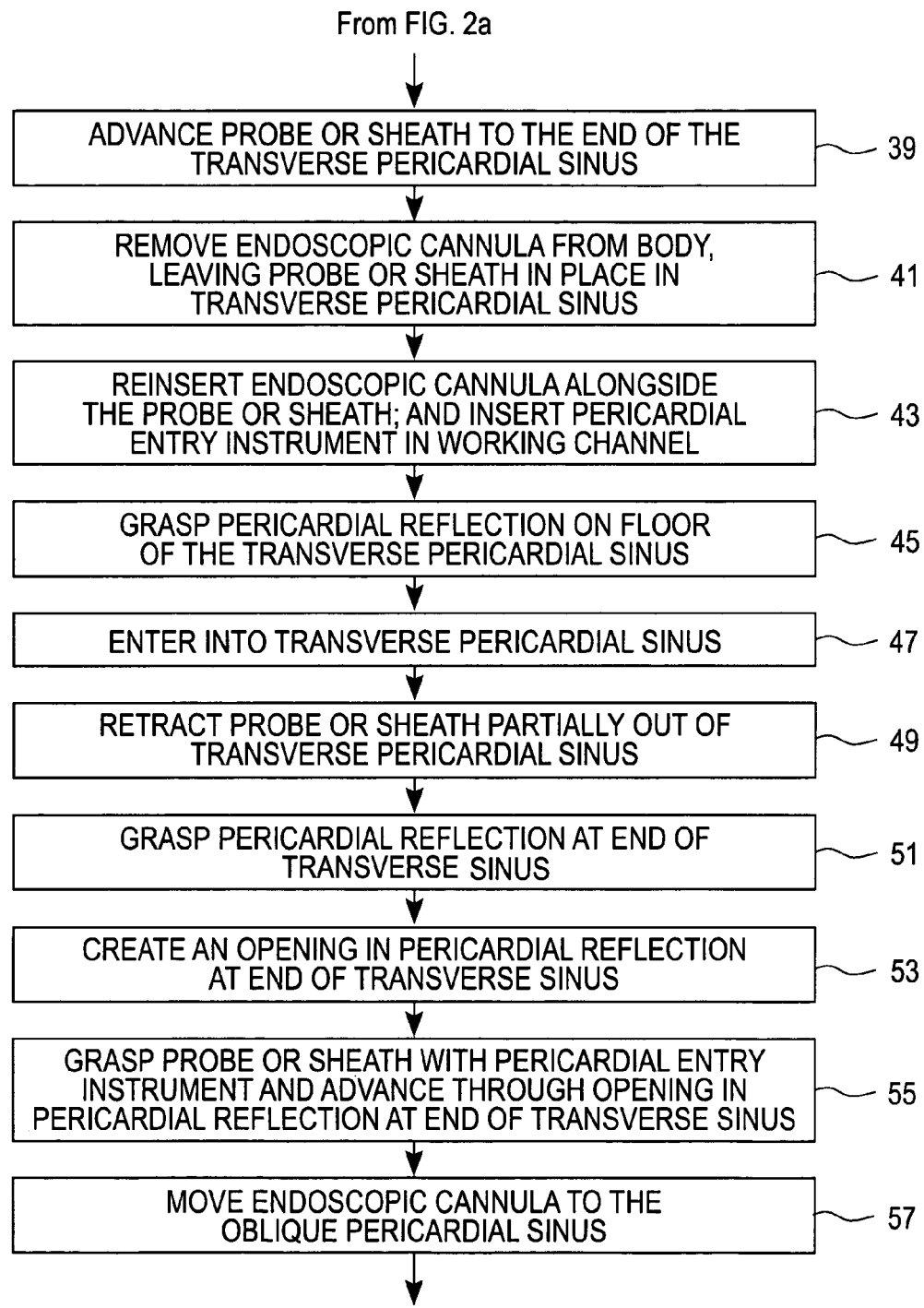
Figure 2C:
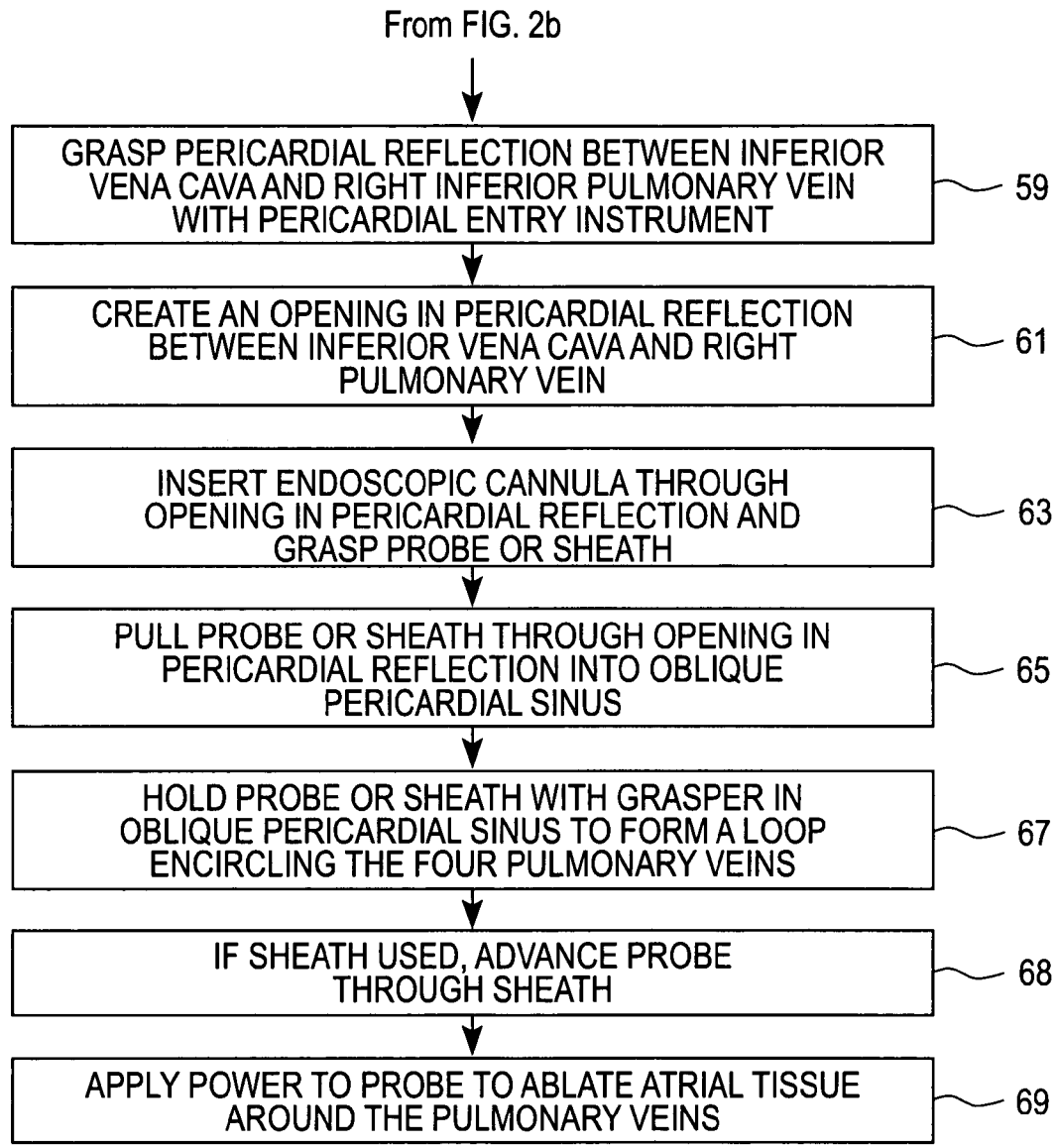

Referring now to the flow chart of FIG. 2, there is shown one procedure for surrounding the pulmonary veins with an ablation probe or sheath. Specifically, the surgical procedure includes forming 17 a subxiphoid skin incision and bluntly dissecting 19 through the incision to expose the linea alba. The linea alba is then excised 21 and a finger is inserted to dissect tissue and thereby form a tract 23 to underside of the xiphoid process and sternum.

Figure 4:
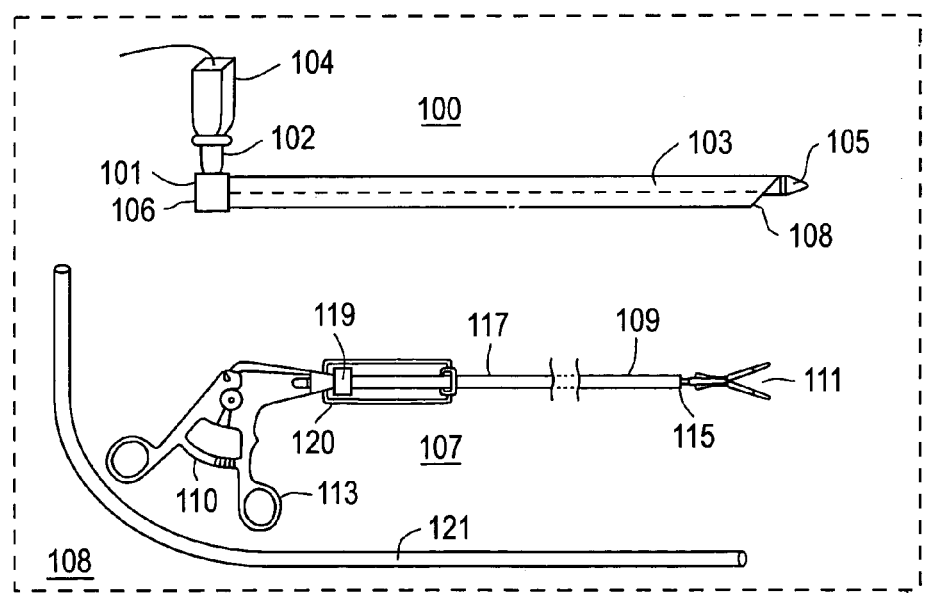
FIG. 4 is a perspective view of a kit of surgical instruments for performing a surgical procedure according to the present invention.

An endoscopic cannula 24, for example as illustrated in FIG. 4, includes a tapered transparent tip 26, and is inserted 25 through the subxiphoid incision 17 and advanced 27 through the diaphragm to the anterior surface of the pericardium. Fat tissue on the anterior surface of the pericardium is bluntly dissected 29 in preparation for entry into the pericardium.

An instrument for forming an entry opening in the pericardium is inserted 31 through a working channel in the endoscopic cannula to grasp 33 a bleb or form a tent of the pericardium near the apex of the heart. An overlying tubular cutter is advanced over the grasped pericardium to cut an opening therethrough for accessing the intrapericardial region.

The endoscopic cannula may now be advanced 35 through the opening cut in the pericardium for inserting 37 through the instrument channel therein an ablation probe or sheath that is then advanced into the transverse pericardial sinus. The ablation probe or sheath therefor is left in place within the transverse pericardial sinus as the endoscopic cannula is removed 41 from the body. The endoscopic cannula may now be reinserted 43 through the subxiphoid incision along side the ablation probe (or sheath) and into the oblique pericardial sinus. An entry instrument is inserted through the working channel of the endoscopic cannula toward the reflection 13 that extends substantially between the right and left superior pulmonary veins, and that therefore forms the base of the transverse pericardial sinus. A bleb or tent of this reflection 13 is grasped 45 and an overlying tubular cutter is rotated through the grasped reflection to form an opening 47 into the transverse pericardial sinus. The ablation probe (or sheath) that was positioned in the transverse pericardial sinus during the procedural step 39 may now be retracted 49 partially from the transverse pericardial sinus.

Next, a bleb or tent of the reflection 11 at the end of the transverse pericardial sinus disposed between the superior vena cava and the right superior pulmonary vein is grasped 51 using the instrument for forming an entry opening in the pericardium that is inserted through a working channel in the endoscopic cannula, and an overlying tubular cutter is rotated to form an opening 53 through the grasped reflections.

Now, the tissue-grasping end effector of the entry instrument may be manipulated through the opening formed in the reflection 13 to grasp the ablation probe (or sheath) to manipulate its advance 55 through the opening formed in the reflection 11. With the probe (or sheath) disposed in the transverse pericardial sinus and through the reflection 13 at the end thereof, the endoscopic cannula, with the entry instrument disposed within the instrument channel, may then be repositioned within the oblique pericardial sinus 57 in order to grasp 59 a bleb or tent of the reflection 9 between the inferior vena cava and the right inferior pulmonary vein using the grasping end effector of the entry instrument. An overlying tubular cutter then cuts the grasped reflection to create an opening 61 in the reflection 9. The endoscopic cannula with the entry instrument disposed in the instrument channel may now be positioned 63 through the opening formed in the reflection 9, and the grasping end effector of the entry instrument is used to grasp the ablation probe (or sheath) extending through the reflection 13. The grasped ablation probe (or sheath) is then pulled through the opening in the reflection 9 into the oblique pericardial sinus 65 where the retrieved end and mid-length of the ablation probe may be linked and grasped to form a loop 67 around the four pulmonary veins. The ablation probe of conventional design thus positioned (or advanced 68 through the sheath to such position) may now be energized 69 to ablate atrial tissue in the looped path surrounding the pulmonary veins.

Figure 3A:
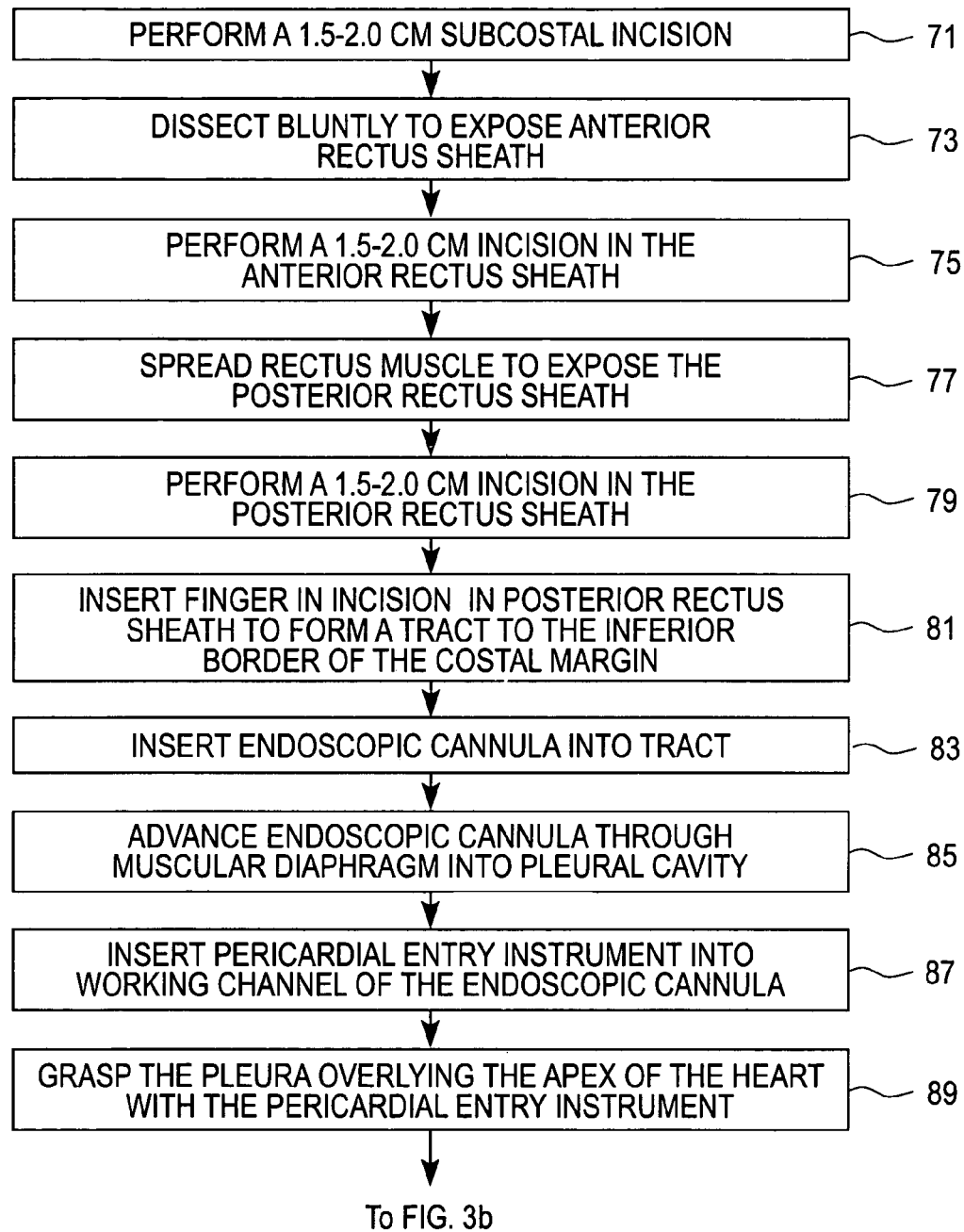
FIGS. 3*a*, *b* comprise a flow chart of a surgical procedure performed in accordance with the present invention via a subcostal entry.
Figure 3B:
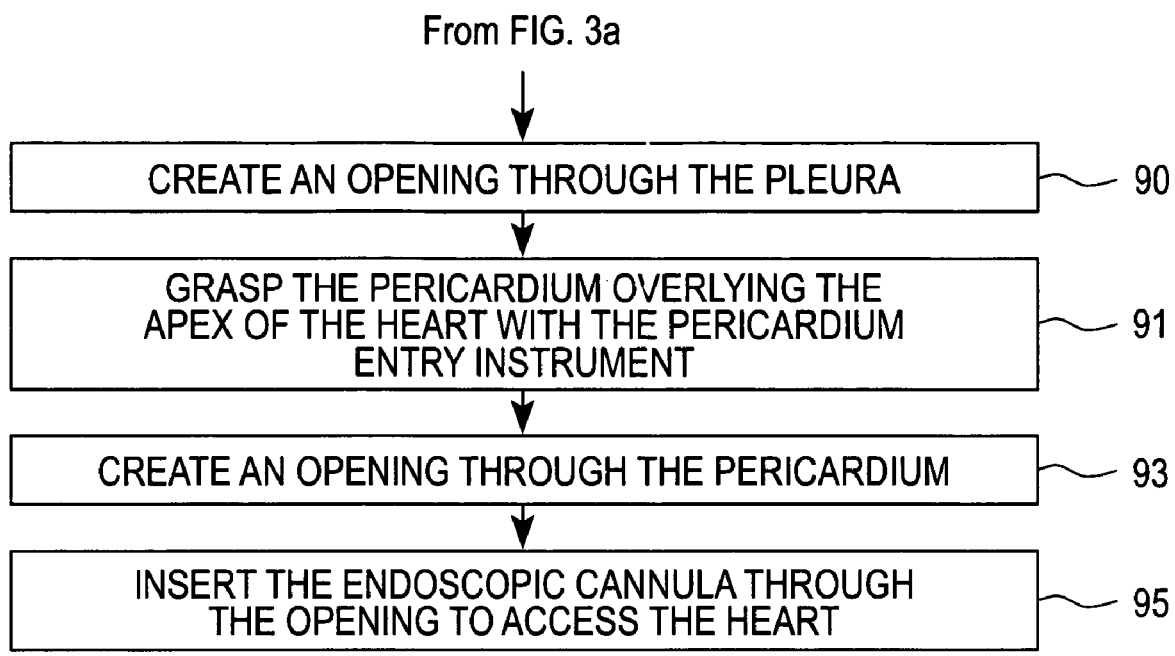

Referring now to the flow chart of FIG. 3, there is shown another method embodiment of the present invention for accessing the heart of a patient in which an initial subcostal entry incision is formed 71. Tissue is then bluntly dissected 73 to expose the anterior rectus sheath, and an incision is formed 75 therein. The rectus muscle is spread 77 to expose the posterior rectus sheath, and an incision 79 is formed therein. Finger dissection of tissue exposed through the incision in the posterior rectus sheath then forms a tract 81 to the inferior border of the costal margin. An endoscopic cannula having an instrument channel therein is inserted 83 into the dissected tissue tract and is advanced through the muscular diaphragm 85 into the pleural cavity. A pericardial entry instrument is inserted into the instrument channel of the endoscopic cannula 87 and is advanced therein toward the apex region of the heart. A bleb or tent of the pleura overlying the heart near the apex region is grasped via the entry instrument 89, and an overlying tubular cutter is advanced through the grasped pleura to form an opening therein 90. The entry instrument may then be advanced through the opening formed in the pleura to grasp a bleb or tent of the pericardium 91 near the apex region of the heart. The overlying tubular cutter is advanced through the grasped pericardium to form an opening 93 in the pericardium. The endoscopic cannula may then be advanced through the opening thus formed in the pericardium 95 to access the regions of the heart, for example, to prepare atrial tissue surrounding the ostia of the four pulmonary veins for ablation substantially in the manner as previously described herein.

Referring now to FIG. 4, there is shown a kit of the surgical instruments assembled for use in positioning an ablation probe (or sheath therefor) about the four pulmonary veins, for example, in the manner as previously described herein. Specifically, the kit 99 includes an endoscopic cannula 100 having an elongated body 103 including an endoscopic lumen 101 and an instrument channel 106 that is disposed eccentric the endoscopic lumen 101 between proximal and distal ends of the body 103. The endoscopic cannula 100 includes a tissue-dissecting transparent tip 105 at the distal end, and an endoscope slidably received in the lumen 101 may include a video camera 102 attached in conventional manner to the eyepiece 104 of the endoscope at the proximal end thereof. The eyepiece and video camera are disposed at right angle relative to the instrument channel 106 to avoid interfering with surgical instruments inserted in the instrument channel 106. The distal end 108 of the instrument channel 106 is chamfered or skewed at an oblique angle relative to the elongated body to facilitate easy entry through pericardial and pleural openings. The proximal end of the instrument channel 106 is displaced from the distal end thereof by a sufficient distance to remain outside of a patient's body during a surgical procedure, for example, as previously described herein in which the distal end of endoscopic cannula is disposed within the intrapericardial region of a patient's heart along a tract through a subxiphoid or subcostal entry incision.

The kit 99 also includes a pericardial entry instrument 107 that includes an elongated body 109 which supports a pair of jaws 111 that are coupled through the body 107 to scissor-like handles 113 mounted at the proximal end of the body 109 for manually controlling the grasping of tissue by the jaws 111. A ratcheting locking mechanism 110 retains the jaws 111 in locked position. The body 109 also supports thereon an overlying tubular cutter 117 having a sharpened distal end 115 and a thumb wheel 119 disposed near the proximal end for manually advancing and rotating the cutting edge through tissue grasped by the jaws 111. Stop mechanism 120 limits the distal extent of translational movement of the tubular cutter 117. The overlying tubular cutter 117 is dimensioned to slide and rotate within the instrument channel 106 of the endoscopic cannula 100. The elongated body 109 has sufficient length to extend through the instrument channel 106 and distally thereof into the visual field of an endoscope disposed within the endoscopic lumen 101. Of course, an endoscope with eyepiece 102 and video camera 104 need not be packaged within the kit 99 but may instead be separately provided in sterile condition for assembly within the endoscopic cannula 100. The kit 99 of instruments may also contain the hollow ablation sheath 121 which may include a guide wire therein. Such guide wire facilitates placement of the sheath around the pulmonary veins with the aid of the instrument channel 106 and grasping jaws 111 of the entry instrument 107, substantially in accordance with the surgical procedure as previously described herein. After placement of the sheath 121 surrounding the pulmonary veins, any guide wire therein may be removed and replaced with a tissue-ablating probe of conventional design that slides within the sheath to substantially surround the pulmonary veins. In operation, with the sheath and ablation probe therein positioned about the pulmonary veins, the ablation probe may be energized in conventional manner to ablate atrial tissue, for example, in a surgical procedure substantially as previously described herein.

The endoscopic cannula 100 and entry instrument 107 and, optionally, the sheath 121 for an ablation probe are packaged in the enclosure 108 that is formed, for example, as an hermetically-sealed carton or envelope to confine the instruments within a sterile environment.

Therefore, the method and surgical instrument in accordance with the present invention greatly facilitate the positioning of a tissue-ablating probe about the pulmonary veins via a subxiphoid or subcostal entry incision, with diminished risk of puncturing the superior vena cava or causing other unintended trauma during a surgical procedure.

What is claimed is:
1. A surgical procedure performed on the heart of a patient, comprising the steps for:
   forming an entry incision on the patient;
   dissecting tissue along a tract from the entry incision toward the patient's heart;
   forming an opening in the pericardium near the apex region and into the intrapericardial space of the patient's heart through the entry incision;
   advancing a surgical instrument through the opening in the pericardium near the apex region and along a path lateral to the left pulmonary veins into the transverse pericardial sinus;
   forming an opening in a first reflection diposed between the left and right superior pulmonary veins;

entering through the opening formed in the first reflection to form an opening in a second reflection disposed between the superior vena cava and the right superior pulmonary vein;

advancing the surgical instrument through the opening formed in the second reflection;

forming an opening in a third reflection disposed between the inferior vena cava and the right inferior pulmonary vein;

advancing the surgical instrument through the opening formed in the third reflection into the oblique pericardial sinus to substantially surround the left and right pulmonary veins with the surgical instrument.

2. The surgical procedure according to claim 1 including:

advancing a tissue-ablating probe within the surgical instrument to substantially surround the left and right pulmonary veins; and energizing the tissue-ablating probe to ablate atrial tissue along the path near the tissue-ablating probe.

3. The surgical procedure according to claim 1 in which the entry incision is formed in the subxiphoid location; and dissecting tissue includes exposing the linea alba within a subxiphoid entry incision, and forming a tract of dissected tissue between the entry incision and the apex region of the patient's heart.

4. The surgical procedure according to claim 1 in which the entry incision is formed at a subcostal location;

dissecting tissue includes exposing the anterior rectus sheath within the subcostal entry incision;

incising the anterior rectus sheath and retracting the rectus muscle to expose the posterior rectus sheath;

incising the posterior rectus sheath to expose the inferior border of the costal margin;

forming a tract through the incisions and the muscular diaphragm into the pleural cavity; and forming an opening through the pleura to expose the pericardium near the apex region of the patient's heart.

5. The surgical procedure according to claim 1 in which forming an opening in one of the first, second and third reflections includes grasping a portion of the reflection; and cutting the grasped portion of the reflection to form an aperture therein.

6. The surgical procedure according to claim 1 in which advancing the surgical instrument through the opening formed in the second reflection includes grasping through the opening formed in the first reflection the surgical instrument positioned within the transverse pericardial sinus for manipulating therein the surgical instrument through the opening formed in the second reflection.

7. The surgical procedure according to claim 1 in which advancing the surgical instrument through the opening formed in the third reflection includes grasping through the opening formed in the third reflection the surgical instrument advanced through the opening formed in the second reflection; and pulling the grasped surgical instrument through the opening formed in the third reflection into the oblique pericardial sinus to substantially complete a loop of the surgical instrument surrounding the left and right pulmonary veins.

8. The surgical procedure according to claim 1 performed with an endoscopic cannula having an instrument channel, the procedure including:

advancing the endoscopic cannula along a path through the entry incision and along the tract of dissected tissue and through the opening formed in the pericardium near the apex region of the patient's heart, and lateral to the left pulmonary veins;

advancing the surgical instrument includes advancing the surgical instrument through the instrument channel of the endoscopic cannula disposed along said path, and into the transverse pericardial sinus;

retracting the endoscopic cannula from along the said path, leaving the surgical instrument disposed within the transverse pericardial sinus;

re-entering the endoscopic cannula through the entry incision and along the tract of dissected tissue and through the opening formed in the pericardium near the apex region, and across the oblique pericardial sinus toward the first reflection; and passing an instrument through the instrument channel of the endoscopic cannula so positioned to form said opening in the first reflection.

9. The surgical procedure according to claim 2 in which a distal end of the surgical instrument is clasped to a portion of the surgical instrument disposed intermediate the opening formed in the pericardium near the apex region and the left pulmonary veins to form a loop of the tissue-ablating probe at least during energization thereof.

\* \* \* \* \*